United States Patent
Tran et al.

(10) Patent No.: US 7,266,676 B2
(45) Date of Patent: Sep. 4, 2007

(54) METHOD AND APPARATUS FOR BRANCH PREDICTION BASED ON BRANCH TARGETS UTILIZING TAG AND DATA ARRAYS

(75) Inventors: Thang M. Tran, Austin, TX (US);
Ravi Pratap Singh, Austin, TX (US);
Deepa Duraiswamy, Austin, TX (US);
Srikanth Kannan, Austin, TX (US)

(73) Assignee: Analog Devices, Inc., Norwood, MA (US)

( * ) Notice: Subject to any disclaimer, the term of this patent is extended or adjusted under 35 U.S.C. 154(b) by 323 days.

(21) Appl. No.: 10/394,820

(22) Filed: Mar. 21, 2003
(Under 37 CFR 1.47)

(65) Prior Publication Data

US 2004/0186985 A1   Sep. 23, 2004

(51) Int. Cl.
*G06F 9/42* (2006.01)
(52) U.S. Cl. ............... 712/238; 712/233; 712/237; 712/239; 712/240
(58) Field of Classification Search ............... 712/233, 712/237, 238, 239, 240
See application file for complete search history.

(56) References Cited

U.S. PATENT DOCUMENTS

| | | | |
|---|---|---|---|
| 5,142,634 A * | 8/1992 | Fite et al. ............... 712/240 |
| 5,608,886 A * | 3/1997 | Blomgren et al. ............... 712/239 |
| 5,732,253 A * | 3/1998 | McMahan ............... 712/239 |
| 5,864,697 A * | 1/1999 | Shiell ............... 712/240 |
| 5,948,100 A * | 9/1999 | Hsu et al. ............... 712/238 |
| 5,964,870 A * | 10/1999 | Malizewski ............... 712/240 |
| 6,119,222 A * | 9/2000 | Shiell et al. ............... 712/238 |
| 6,389,531 B1 | 5/2002 | Irle et al. |

OTHER PUBLICATIONS

Jackson, R.T. and F.O. Karim, Branch Anticipation and Prediction Algorithm, Dec. 1992, IBM Technical Disclosure Bulletin, vol. 35, No. 7, p. 73-74.*

* cited by examiner

*Primary Examiner*—Vincent Lai
(74) *Attorney, Agent, or Firm*—Wolf, Greenfield & Sacks, P.C.

(57) ABSTRACT

Methods and apparatus are provided for branch prediction in a digital processor. A method includes providing a branch target buffer having a tag array and a data array, wherein each entry in the tag array provides an index to a corresponding entry in the data array, storing in a selected entry in the tag array information representative of a branch target of a current branch instruction, storing in a corresponding entry in the data array information representative of a branch target of a next branch instruction, and providing the information representative of the branch target of the next branch instruction in response to a match to an entry in the tag array. The information representative of the branch target of the next branch instruction may include a taken branch target address of the next branch instruction and an offset value. The offset value may represent an address of a next sequential instruction following the next branch instruction.

30 Claims, 12 Drawing Sheets

| Tag Array | | Data Array | | | |
|---|---|---|---|---|---|
| LRU/Valid Bits | Tag Address | Target Address | Offset | Branch Type | Prediction Bits |
| | A | B | Addr of Instr 5 | Conditional | Taken |
| | B | E | Addr of Instr 27 | Conditional | Not Taken |
| | C | D (Not Shown in Fig) | Addr of Instr 29 | Conditional | Taken |

FIG. 4B

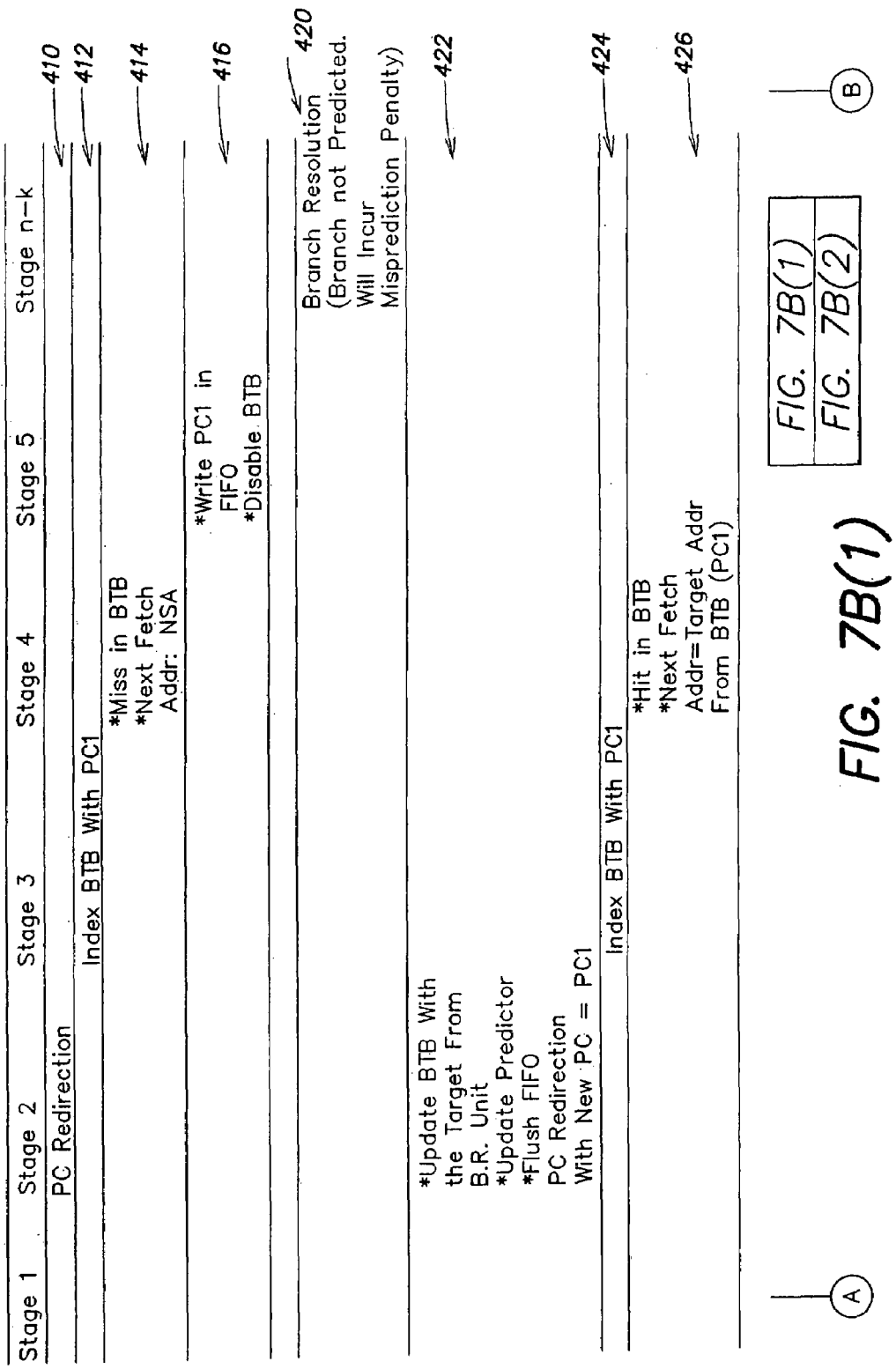
FIG. 7B(1)

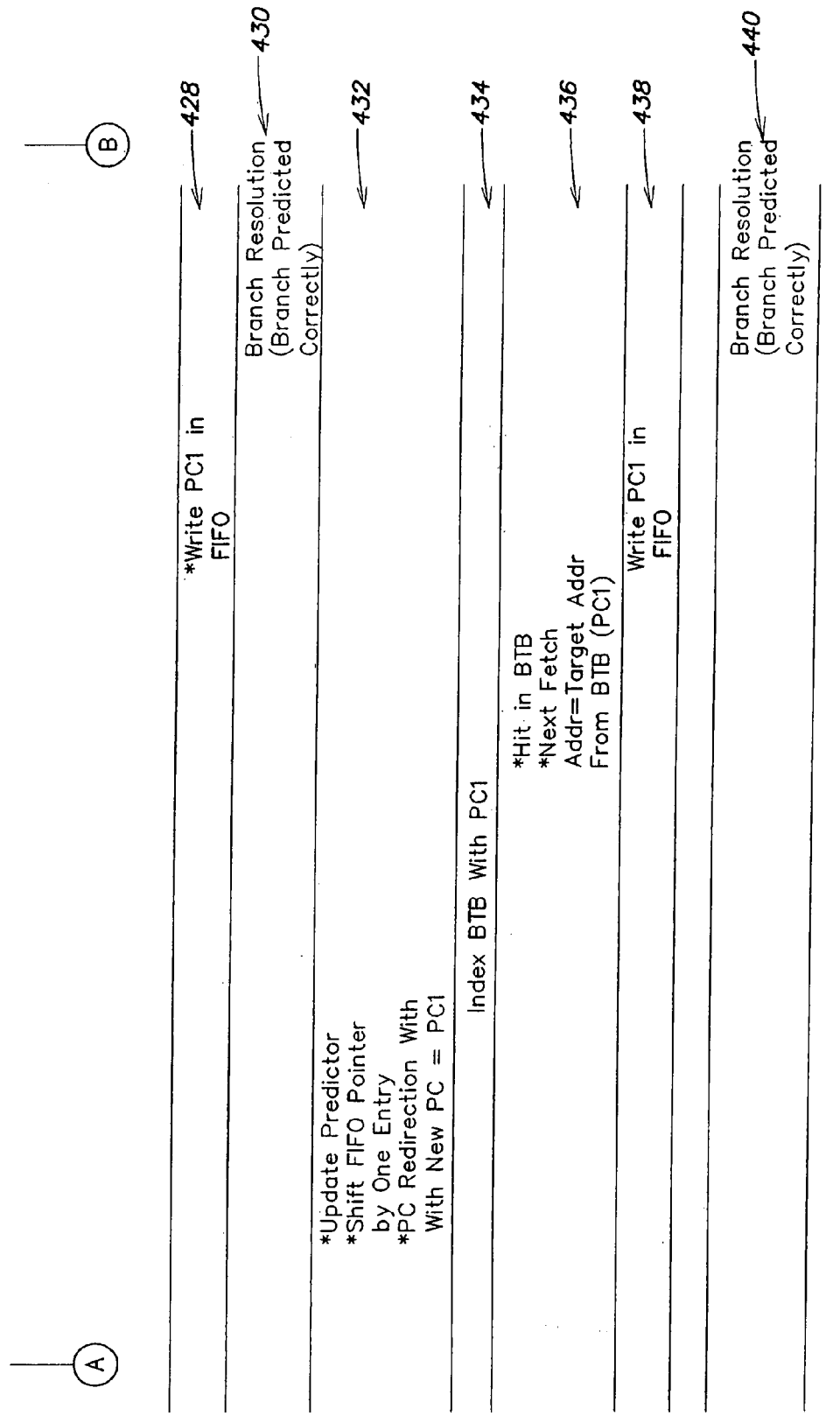
FIG. 7B(2)

METHOD AND APPARATUS FOR BRANCH PREDICTION BASED ON BRANCH TARGETS UTILIZING TAG AND DATA ARRAYS

FIELD OF THE INVENTION

This invention relates to digital processors and, more particularly, to methods and apparatus for improving digital processor performance by predicting branches based on branch targets.

BACKGROUND OF THE INVENTION

A digital signal computer, or digital signal processor (DSP), is a special purpose computer that is designed to optimize performance for digital signal processing applications, such as, for example, fast Fourier transforms, digital filters, image processing, signal processing in wireless systems, and speech recognition. Digital signal processor applications are typically characterized by real-time operation, high interrupt rates and intensive numeric computations. In addition, digital signal processor applications tend to be intensive in memory access operations and to require the input and output of large quantities of data. Digital signal processor architectures are typically optimized for performing such computations efficiently. In addition to digital signal processor applications, DSPs are frequently required to perform microcontroller operations. Microcontroller operations involve the handling of data but typically do not require extensive computation.

Digital signal processors may utilize a pipelined architecture to achieve high performance. As known in the art, a pipelined architecture includes multiple pipeline stages, each of which performs a specified operation, such as instruction fetch, instruction decode, address generation, arithmetic operations, and the like. Program instructions advance through the pipeline stages on consecutive clock cycles, and several instructions may be in various stages of completion simultaneously.

Performance can be enhanced by providing a large number of pipeline stages. The number of pipeline stages in a processor is sometimes referred to as pipeline depth. Notwithstanding the enhanced performance provided by pipelined architectures, certain program conditions may degrade performance. An example of such a program condition is a branch instruction. Branch instructions are common in most computer programs, including for example digital signal processor applications and microcontroller applications. When a branch instruction advances through a pipelined processor and branch prediction is not utilized, sequential instructions follow the branch instruction in the pipeline. If the branch is taken, the pipeline must be drained by aborting all instructions currently in the pipeline and re-executing instructions from the branch target. The branch performance penalty is proportional to the depth of the pipeline. For deeply pipelined architectures and programs having frequent branch instructions, the performance penalty is severe.

Branch prediction techniques are known in the art. In a typical prior art approach, a branch cache contains the addresses of branch instructions and corresponding prediction information. When a branch instruction is fetched, the prediction information is used to estimate if the branch will be taken.

Prior art branch prediction techniques have had drawbacks and disadvantages including, but not limited to, excessive complexity and power consumption, and limited impact on performance. Accordingly, there is a need for improved methods and apparatus for branch prediction in digital processors.

SUMMARY OF THE INVENTION

According to a first aspect of the invention, a method is provided for branch prediction in a digital processor. The method comprises providing a branch target buffer having a tag array and a data array, wherein each entry in the tag array provides an index to a corresponding entry in the data array, storing in a selected entry in the tag array information representative of a branch target of a current branch instruction, storing in a corresponding entry in the data array information representative of a branch target of a next branch instruction, and providing the information representative of the branch target of the next branch instruction in response to a match to an entry in the tag array.

The step of storing information representative of a branch target of a current branch instruction may comprise storing a taken branch target address of the current branch instruction in the case of a taken branch. The step of storing information representative of a branch target of a current branch instruction may comprise storing an address of a next sequential instruction following the current branch instruction in the case of a not taken branch.

The step of storing information representative of a branch target of a next branch instruction may comprise storing a taken branch target address of the next branch instruction and a not taken branch target address of the next branch instruction. The not taken branch target address may comprise an offset value which represents an address of a next sequential instruction following the next branch instruction.

The method may further comprise performing a block size calculation by subtracting the offset value from a current fetch address and redirecting instruction fetching to the branch target buffer when the difference between the offset value and the current fetch address is less than a predetermined value. The predetermined value may represent the length of a fetch buffer.

The step of storing information representative of a branch target of a next branch instruction may comprise storing prediction information corresponding to the next branch instruction. The prediction information may be updated following execution of the next branch instruction. A taken branch target address of the next branch instruction or a next sequential address may be selected in response to the prediction information.

According to another aspect of the invention, apparatus is provided for predicting branches in a program executed on a digital processor. The apparatus comprises a branch target buffer having a tag array and a data array, wherein each entry in the tag array provides an index to a corresponding entry in the data array, means for storing in a selected entry in the tag array information representative of a branch target of a current branch instruction, means for storing in a corresponding entry in the data array information representative of a branch target of a next branch instruction, and means for providing from the branch target buffer the information representative of the branch target of the next branch instruction in response to a match to an entry in the tag array.

According to a further aspect of the invention, apparatus is provided for predicting branches in a program executed on a digital processor. The apparatus comprises a branch target buffer having a tag array and a data array, wherein each entry in the tag array provides an index to a corresponding entry in the data array, wherein a selected entry in the tag array stores information representative a branch target of a current branch instruction and a corresponding entry in the data array stores a taken branch target address of a next branch instruction, a not taken branch target address of the next branch instruction and prediction information corresponding to the next branch instruction, an address selector for selecting the taken branch target address or the not taken branch target address in response to the prediction information, and a block size calculation unit for redirecting instruction fetching to the branch target buffer when the difference between the not taken branch target address and the current fetch address is less than a predetermined value.

BRIEF DESCRIPTION OF THE DRAWINGS

For a better understanding of the present invention, reference is made to the accompanying drawings, which are incorporated herein by reference and in which:

FIG. 4B is a table that illustrates contents of a branch target buffer for the program segments of FIG. 4A, in accordance with an embodiment of the invention;

FIGS. 7B and 7C illustrate execution of the program segment of FIG. 7A in a pipelined processor, in accordance with an embodiment of the invention.

DETAILED DESCRIPTION

Figure 1:
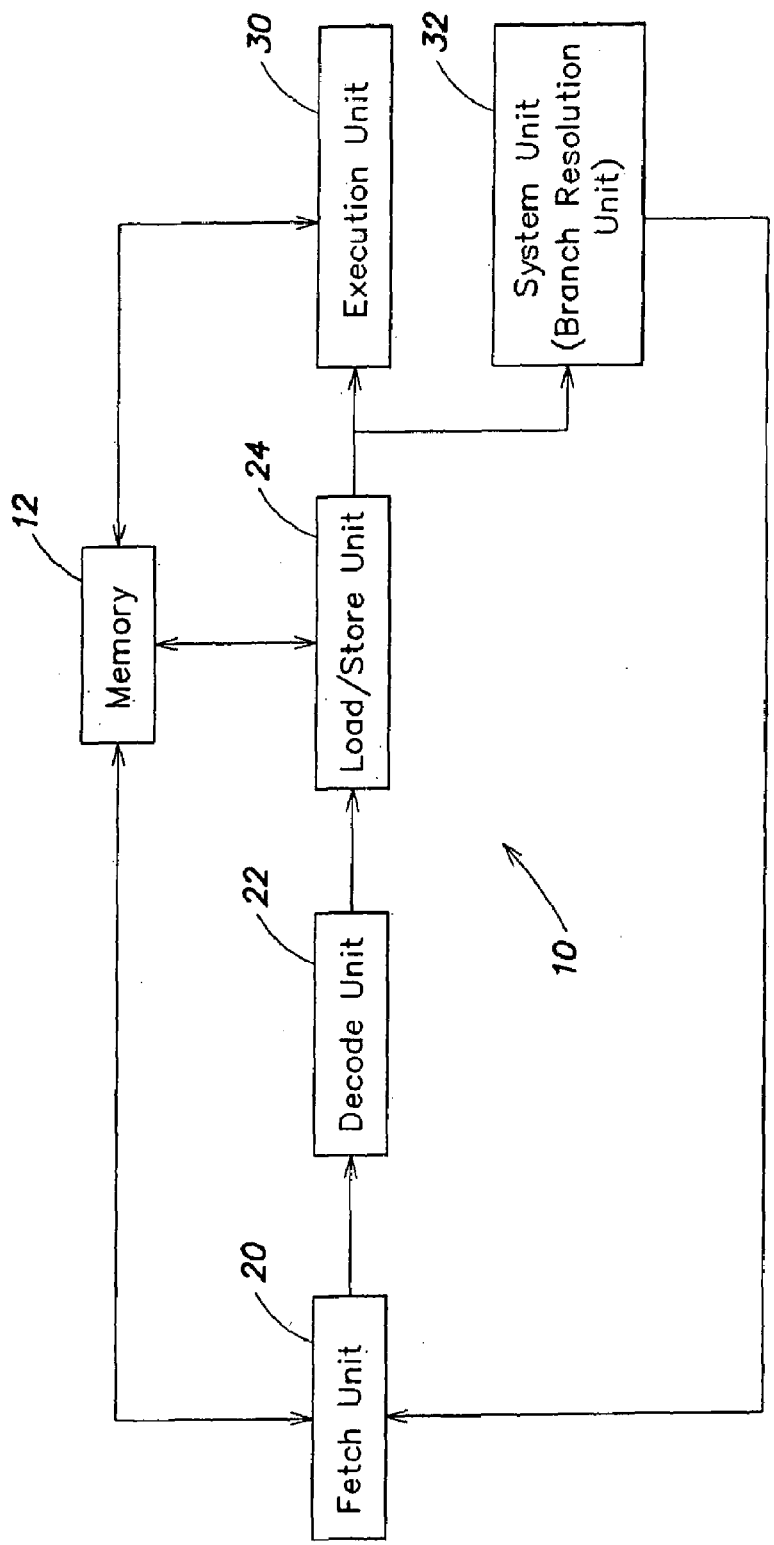
FIG. 1 is a block diagram of a digital processor having a pipelined architecture.

A block diagram of an embodiment of a digital signal processor (DSP) is shown in FIG. 1. The digital signal processor includes a computation core 10 and a memory 12. The computation core is the central processor of the DSP. The core 10 and the memory 12 may have a pipelined architecture, as described below. In this embodiment, core 10 includes an instruction fetch unit 20, an instruction decode unit 22, a load/store unit 24, an execution unit 30 and a system unit 32, which may include a branch resolution unit.

The instruction fetch unit 20 and the instruction decode unit 22 are discussed below. Load/store unit 24 controls access to memory 12. Memory read data may be transferred from memory 12 to a register file in execution unit 30. Memory write data may be transferred from the register file in execution unit 30 to memory 12. Instruction fetch unit 20 may access memory 12 in the case of an instruction cache miss in fetch unit 20. System unit 32 provides branch resolution information to instruction fetch unit 20 as described below. Execution unit 30 may include adders, multipliers, accumulators, shifters, etc. as needed for instruction execution.

Figure 2:
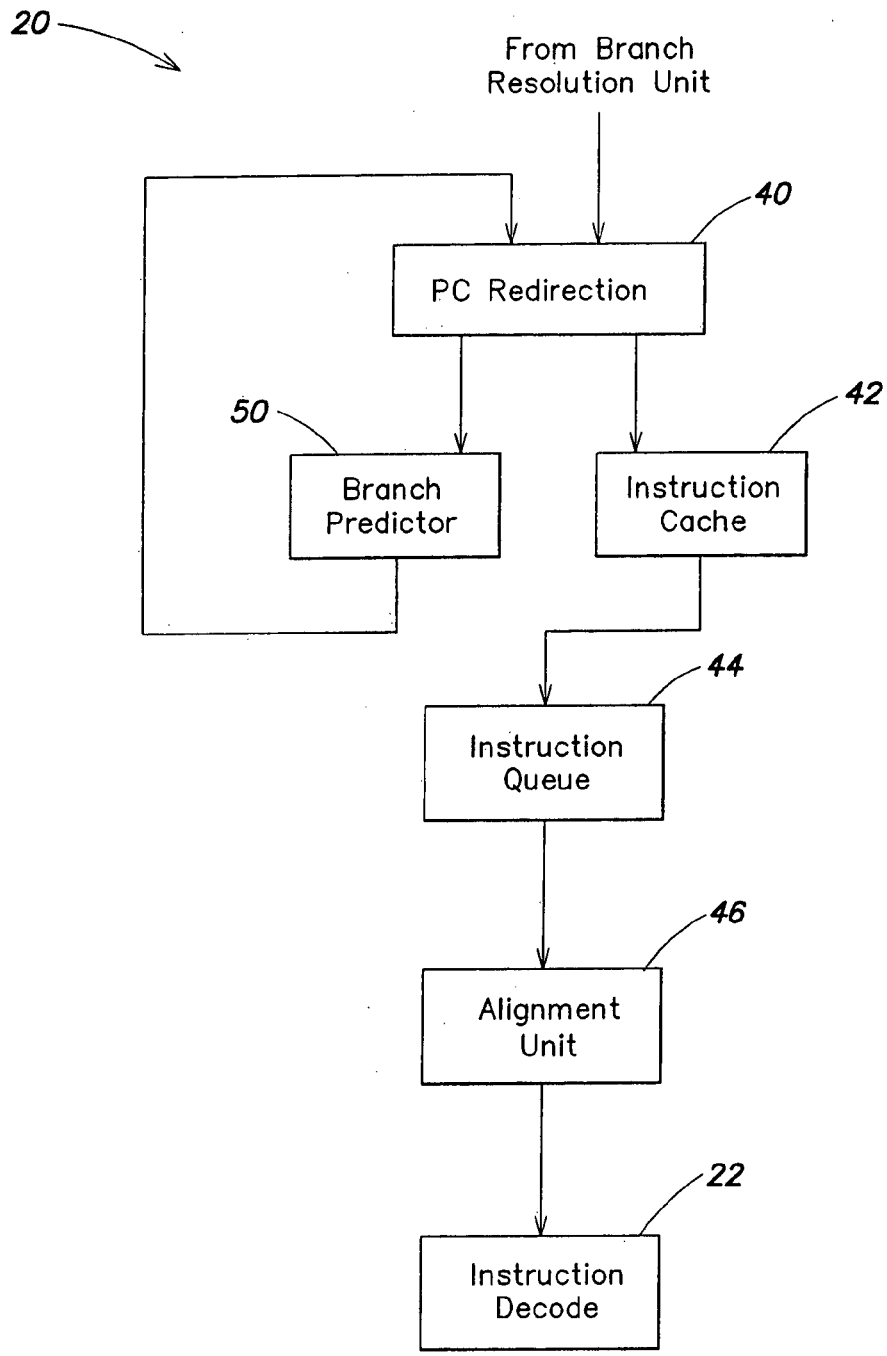
FIG. 2 is a simplified block diagram of the fetch unit and decode unit shown in FIG. 1.

A simplified block diagram of instruction fetch unit 20 and instruction decode unit 22 is shown in FIG. 2. Instruction fetch unit 20 may include a PC (Program Counter) redirection unit 40, an instruction cache 42, an instruction queue 44, an instruction alignment unit 46 and a branch predictor 50. The PC redirection unit 40 determines the addresses of the instructions to be fetched. Program instructions are fetched from the instruction cache 42, are placed in instruction queue 44 and are aligned by alignment unit 46. The aligned instructions are decoded by instruction decoder 22, and the decoded instructions are passed to the load/store unit 24 (FIG. 1). In the event of an instruction cache miss, the requested instruction is accessed in memory 12 (FIG. 1). During normal program flow, a program counter is incremented to generate sequential instruction addresses. Branch predictor 50 operates as described in detail below to predict branch instructions and to redirect instruction fetching so as to limit adverse effects on performance. After the branch instruction has been executed, branch resolution information is provided from system unit 32 (FIG. 1).

The computation core 10 preferably has a pipelined architecture. The pipelined architecture is a well-known architecture wherein the core includes a series of connected stages that operate synchronously, and instruction execution is divided into a series of operations performed in successive pipeline stages in successive clock cycles. Thus, for example, a first stage may perform instruction fetch, a second stage may perform instruction decoding, a third stage may perform data address generation, a fourth stage may perform data memory access and a fifth stage may perform the specified computation. An advantage of the pipelined architecture is increased operating speed, since multiple instructions may be in process simultaneously, with different instructions being in different stages of completion. It will be understood that each of the units shown in FIG. 1 may include one or more pipeline stages. By way of example only, the computation core 10 may include up to 30 stages.

Figure 3:
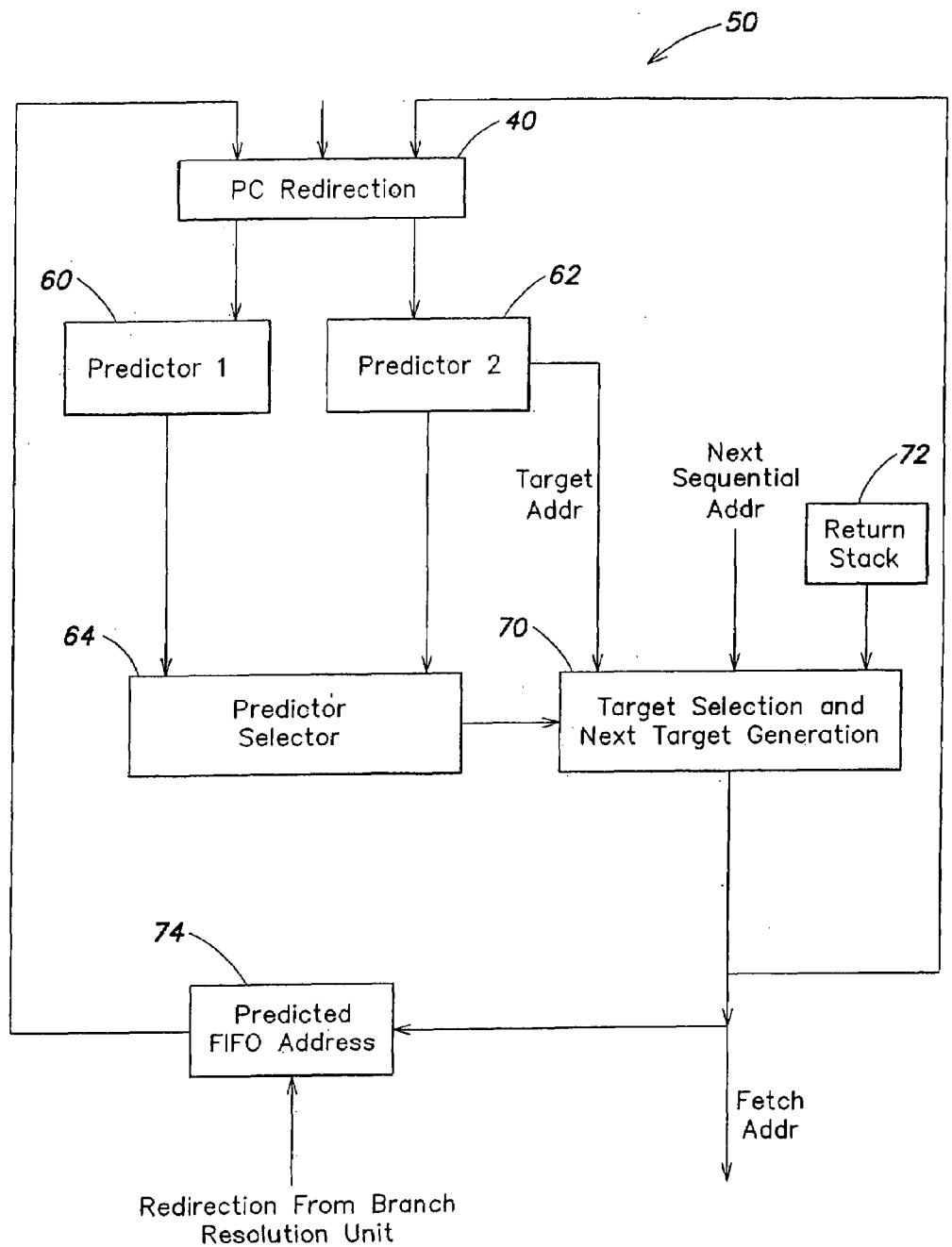
FIG. 3 is a simplified block diagram of the branch predictor of FIG. 2.

Branch predictor 50 is shown in more detail in FIG. 3. A redirected PC address is supplied to a first predictor 60 and to a second predictor 62. Each of predictors 60 and 62 may contain prediction information indicative of whether each branch will be taken or not taken when a corresponding branch instruction is executed. The prediction information in predictors 60 and 62 may be based on different criteria. The outputs of predictors 60 and 62 are supplied to a predictor selector 64. Predictor 62 also supplies a target address to a target selection unit 70. Target selection unit 70 further receives a next sequential address and a return address from a return stack 72. One of the fetch addresses is selected by target selection unit 70 in accordance with the output of predictor selector 64. The fetch address is supplied to an input of PC redirection unit 40 and to the input of a predicted address FIFO 74. The output of FIFO 74 is supplied to PC redirection unit 40. FIFO 74 is controlled by a redirection signal from branch resolution unit 32 (FIG. 1).

Figure 4A:
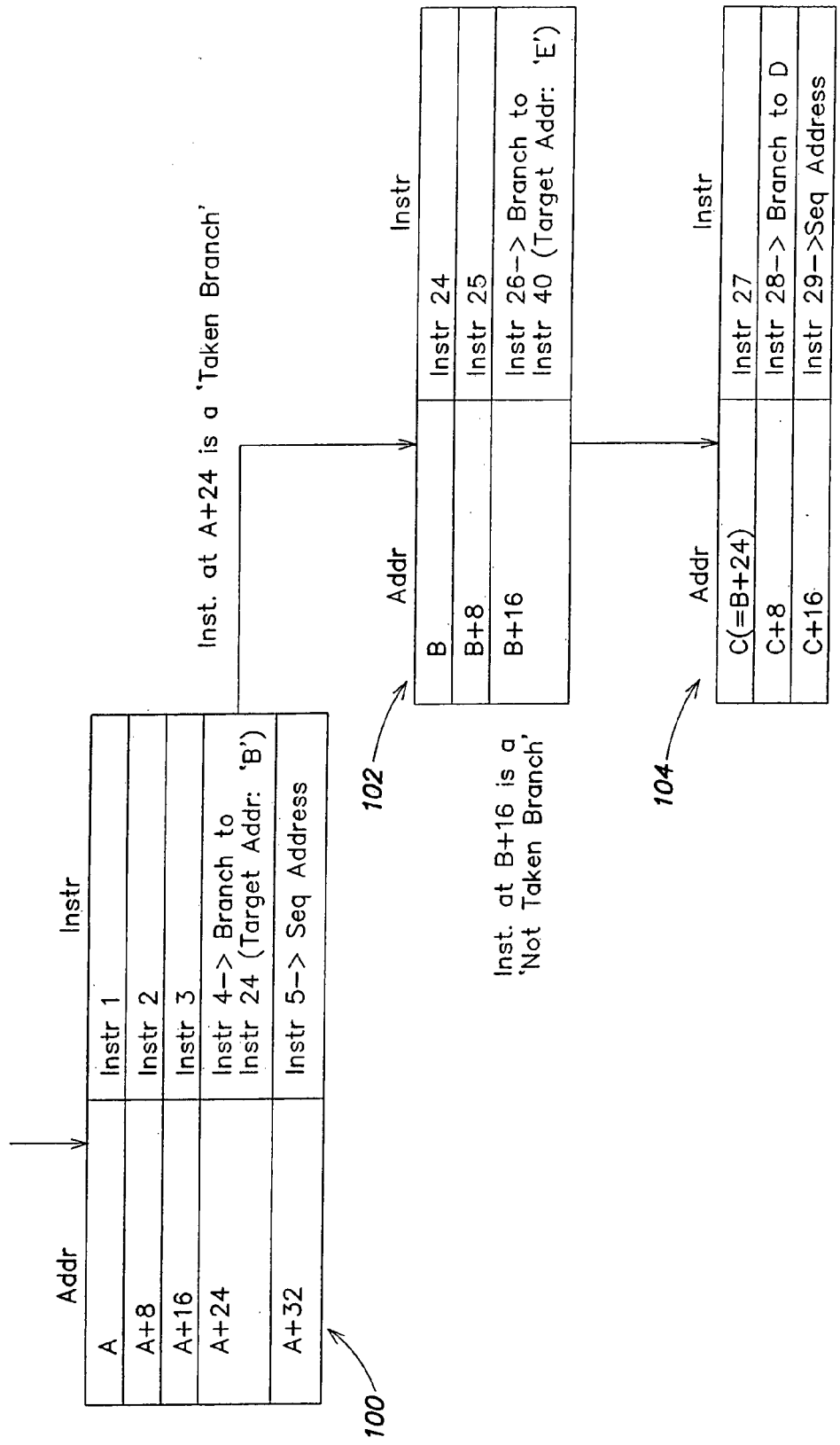
FIG. 4A is a schematic diagram that illustrates an example of program segments which include branch instructions.

FIG. 4A is a schematic diagram that illustrates an example of program segments containing branch instructions. Each program segment includes a series of instructions and corresponding instruction addresses. A program segment 100 includes instructions 1 through 5 at addresses A through A+32, respectively. Instruction 1 at address A is the target of a previous branch instruction. Program segment 100 includes a branch instruction 4 at address A+24. A program segment 102 includes instructions 24 through 26 at addresses B through B+16, respectively. Program segment 102 includes a branch instruction 26 at address B+16. A program segment 104 includes instructions 27 through 29 at addresses C through C+16, respectively. Program segment 104 includes a branch instruction 28 at address C+8. Branch instruction 4 in program segment 100 targets instruction 24 at address B in program segment 102. Branch instruction 26 in program segment 102 targets instruction 40 at address E. Branch instruction 28 in program segment 104 targets an instruction (not shown) at address D.

Each branch instruction in FIG. 4A is a conditional branch. If a condition specified by the branch instruction is met, the branch is taken and a target instruction, referred to as a "taken branch target", is fetched. If the condition is not met, the next sequential instruction following the branch instruction, referred to as a "not taken branch target", is fetched. A "taken branch target address" corresponds to the taken branch target, and a "not taken branch target address" corresponds to the not taken branch target.

In accordance with an aspect of the invention, branch predictor 50 shown in FIG. 2 includes a branch target buffer. The branch target buffer (BTB) has a structure similar to a cache memory, including a tag array and a data array. Each entry in the BTB includes a tag entry and a corresponding data entry. The tag entry and the data entry may each include one or more fields. Each tag entry includes a tag address which corresponds to the upper order bits of an instruction address. The tag address serves as an index to the corresponding data entry. When an input instruction address matches a tag address, a BTB hit occurs and the corresponding data entry is accessed.

In accordance with an embodiment of the invention, each entry in the BTB may include the following fields. The tag entry may include a tag address field which contains the address of the target instruction of the current branch instruction, based on prediction information as discussed below. In the case of a taken branch, the tag address is the taken branch target address of the current branch instruction. In the case of a not taken branch, the tag address is the address of the instruction that follows the current branch instruction. The tag entry may also include a valid field and a LRU (least recently used) field. In one example, the tag address field includes 23 bits (bits 31:9 of the address), the valid field includes one bit and the LRU field includes 6 bits. It will be understood that these fields and field sizes are given by way of example only and are not limiting as to the scope of the invention. Different tag entry fields and field sizes may be utilized within the scope of the invention.

The corresponding data entry may include information representative of a branch target of a next branch instruction. The next branch instruction is one that follows the current branch instruction and may be separated from the current branch instruction by any number of sequential instructions. The data entry may include a target address field, an offset field, and a prediction field. The target address field may include the taken branch target address of the next branch instruction. The offset field may include the low order address bits of the next sequential instruction following the next branch instruction. In one embodiment, the prediction field may include two bimodal prediction bits, which may have values of strongly taken, weakly taken, weakly not taken or strongly not taken. It will be understood that a variety of different predictors may be utilized. Additional fields in each data entry may include an overflow field, a branch type field and a user/supervisor field. The overflow field may include an offset overflow bit which indicates overflow of the offset value into the next instruction cache page. The branch type field may include branch type bits, which may represent call, return, unconditional branch or conditional branch. In one example, the target address field includes 31 bits, the offset field includes 6 bits, the overflow field includes one bit, the prediction field includes two bits, the user/supervisor field includes one bit, and the branch type field includes two bits. It will be understood that these fields and field sizes are given by way of example only and are not limiting as to the scope of the invention. Different data entry fields and field sizes may be utilized within the scope of the invention.

The size of the BTB may be based on the size of the instruction cache. Preferably, the BTB should provide prediction for all branches in the instruction cache. In one embodiment, the BTB has 1 K entries for an instruction cache size of 32 K bytes. It will be understood that other BTB sizes and techniques for determining BTB size may be utilized within the scope of the invention.

Referring now to FIG. 4B, a portion of a branch target buffer 110 is shown. BTB 110 includes a tag array 112 and a data array 114. Entry 120 in BTB 110 includes target address A in the tag address field of tag array 112, target address B in the target address field of data array 114, the address of instruction 5 in the offset field of data array 114, "conditional" in the branch type field of data array 114 and "taken" in the prediction field of data array 114. Similarly, entry 122 in BTB 100 includes target address B in the tag address field of tag array 112 and target address E in the target address field of data array 114. In addition, entry 122 includes the address of instruction 27 in the offset field, "conditional" in the branch type field and "not taken" in the prediction field of data array 114. It may be observed that instruction address B is the next target address in entry 120 and is the current target address in entry 122 for the case where instruction 4 is a taken branch. Entry 124 in BTB 110 includes, in the tag address field of tag array 112, next sequential address C following branch instruction 26, for the case where branch instruction 26 is a not taken branch. Entry 124 also includes target address D of branch instruction 28 in the target address field of data array 114 and the address of instruction 29 in the offset field of data array 114. In each case, the target address field of data array 114 contains the taken branch target address of the next branch instruction and the offset field of data array 114 contains the not taken branch target address of the next branch instruction.

Figure 5:
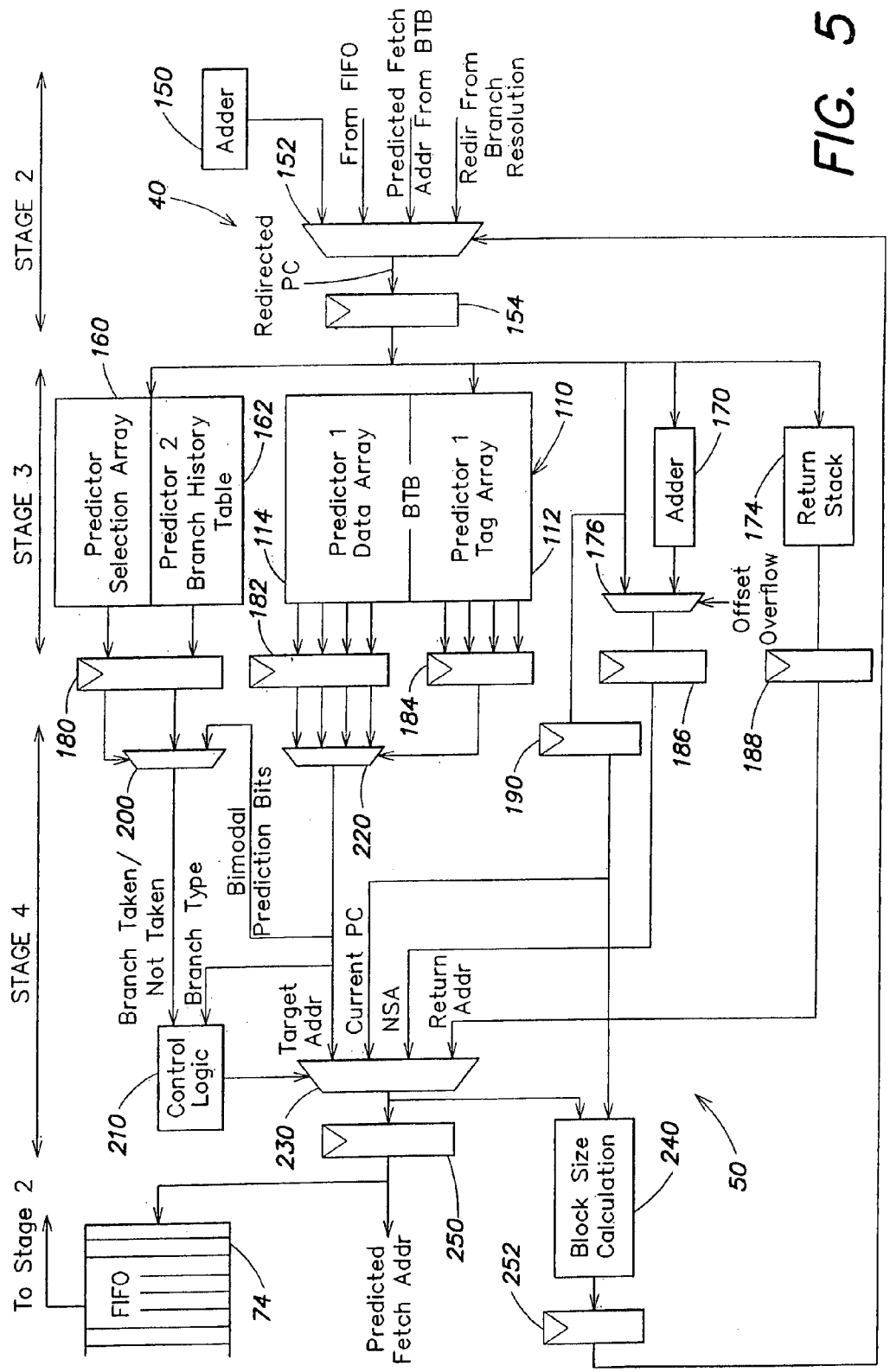
FIG. 5 is a block diagram of an embodiment of the branch predictor.

A block diagram of an embodiment of branch predictor 50 is shown in FIG. 5. A pipeline architecture is illustrated. In particular, stages 2, 3 and 4 of a pipelined processor are shown. Stage 1 (not shown) may include a translation lookaside buffer (TLB) for translating virtual addresses to physical addresses. Stage 2 may include an adder 150, an address selector 152 and a stage 2 latch 154. Adder 150 supplies sequential instruction addresses to address selector 152 during sequential instruction fetching. Address selector 152 also receives instruction addresses from FIFO 74, a predicted fetch address from branch target buffer 110 and a redirection address from branch resolution unit 32 (FIG. 1). A redirected PC address is output from address selector 152 and is held in stage 2 latch 154.

The output of stage 2 latch 154 is supplied to stage 3, which includes a predictor selection array 160, a branch history table 162 (predictor 2), branch target buffer 110, an adder 170 and a return stack 174. As described above, branch target buffer 110 includes tag array 112 and data array 114 (predictor 1). Stage 3 further includes an address selector 176 which selects the output of latch 154 or the output of adder 170 in response to the offset overflow bit. The outputs of predictor selection array 160 and branch history table 162 are held in a stage 3 latch 180. The outputs of BTB data array 114 are held in a stage three latch 182, and the outputs of BTB tag array 112 are held in a stage 3 latch 184. The output of address selector 176 is held in a stage 3 latch 186, and the output of return stack 174 is held in a stage 3 latch 188. The current PC address from latch 154 is held in a stage 3 latch 190.

The outputs of stage 3 latches 180, 182, 184, 186 and 188 are supplied to stage 4. Stage 4 includes a predictor selector 200, control logic 210, a data entry selector 220, an address selector 230 and a block size calculation unit 240.

In the example of FIG. 5, branch target buffer 110 has a cache structure including four ways. An input address to tag array 112 may or may not match one of the tag array entries. When the input address does not match a tag array entry, a BTB miss occurs and sequential fetching resumes. When the input address matches a tag array entry in one of the ways, a BTB hit occurs and the tag array 112 supplies a match signal via latch 184 to the select input of data entry selector 220. Data entry selector 220 receives the outputs of the ways of data array 114 via latch 182 and is controlled by the match signal from tag array 112 to provide a data entry from data array 114 in BTB 110. The selector 220 outputs the data entry selected by the match signal.

The data entry output by selector 220 includes a target address, which is supplied to an input of address selector 230, an offset, prediction bits, which are supplied to a first input of predictor selector 200, and a branch type, which is supplied to control logic 210. Address selector 230 receives the target address from data entry selector 220, a current PC address from stage 3 latch 190, a next sequential address (NSA) from stage 3 latch 186 and a return address from stage 3 latch 188.

Prediction bits from branch history table 162 are supplied via latch 180 to a second input of predictor selector 200, and a prediction selection signal from predictor selection array 160 is supplied via latch 180 to a selection input of predictor selector 200. Selector 200 selects prediction bits from data array 114 (predictor 1) or from branch history table 162 (predictor 2) and outputs a branch taken/not taken signal to control logic 210.

Control logic 210 receives the branch taken/not taken signal and the branch type signal and provides a select signal to address selector 230. In the case of a conditional branch, control logic 210 selects the target address or the next sequential address according to the branch taken/not taken signal. In the case of a return instruction, the return address is selected. In the case of sequential instruction fetching, the current PC address is selected.

The output of address selector 230 is supplied to a stage 4 latch 250 and to block size calculation unit 240. Block size calculation unit 240 also receives the current PC address from stage 3 latch 190. The output of block size calculation unit 240 is supplied to a stage 4 latch 252. The output of stage 4 latch 252 provides a control input to address selector 152 in stage 2.

The output of stage 4 latch 250 is supplied to FIFO 74, which is part of stage 5. FIFO 74 holds the data entry in data array 114 for each branch instruction that is pending in the pipeline. Upon branch resolution, the information in FIFO 74 is used to update BTB 110. When the BTB 110 is updated following branch resolution, current target information is provided by branch resolution unit 32 (FIG. 1) and next target information is provided by FIFO 74.

The block size calculation unit 240 determines when the BTB 110 is to be accessed based on the offset value from the most recent BTB access. The offset value contains the low order bits of the next sequential address after the next branch instruction. The block size calculation unit 240 compares the current fetch address with the offset value to determine when the BTB 110 should be accessed. Each access to instruction cache 42 fetches four 16-bit words, or eight bytes. When the difference between the current fetch address and the offset value is less than eight bytes, the current fetch address is the address of the next branch instruction. Thus, when the difference between the current fetch address and the offset value is less than 8, redirection to branch target buffer 110 is initiated by block size calculation unit 240.

Figure 6:
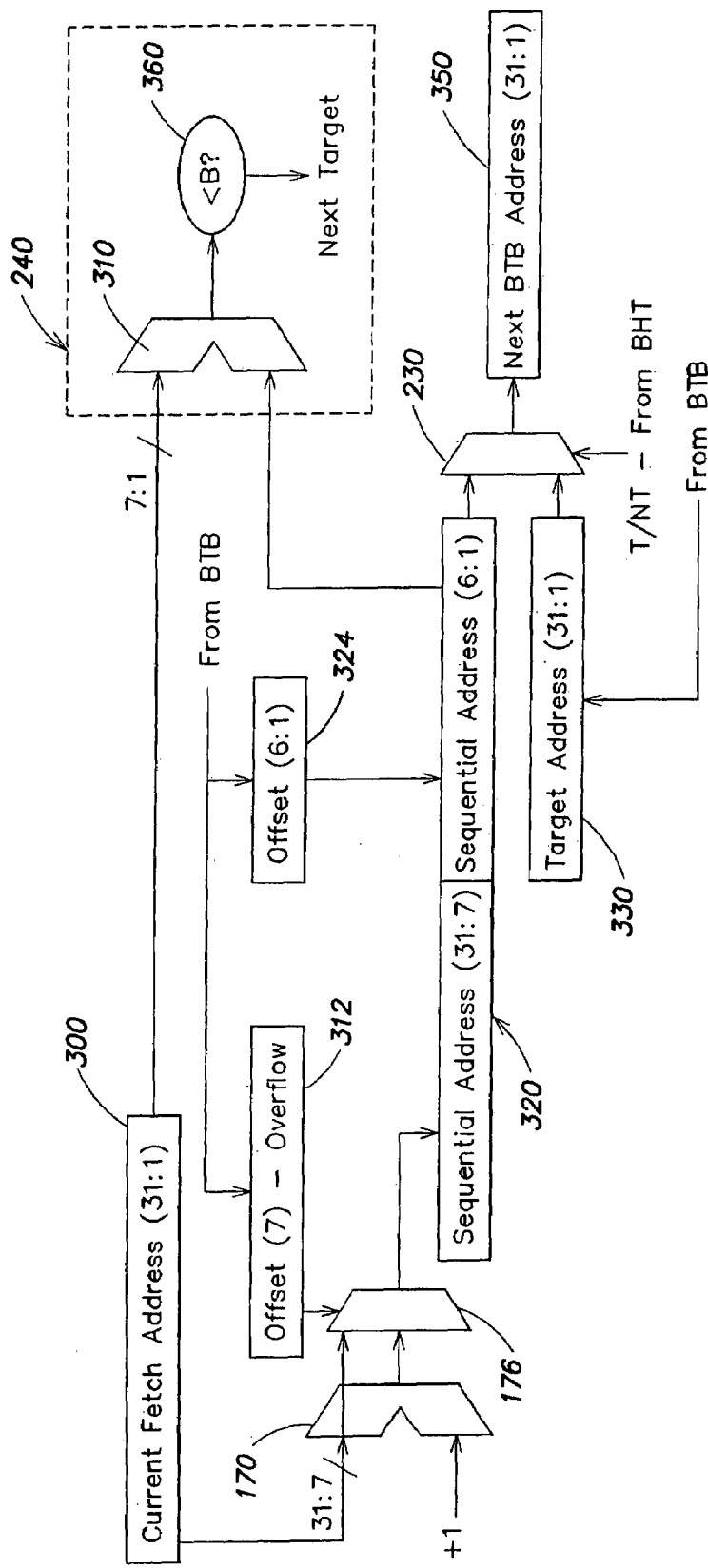
FIG. 6 is a block diagram of an embodiment of the block size calculation unit shown in FIG. 5.

A schematic block diagram that illustrates an embodiment of an algorithm for generating the next fetch address is shown in FIG. 6. Like elements in FIGS. 5 and 6 have the same reference numerals. A current fetch address 300 may include bits (31:1) in the case of a 32-bit instruction address. The high order bits (31:7) of current fetch address 300 are supplied to a first input of adder 170 and to a first input of address selector 176. The adder 170 adds one to the high order bits of current fetch address 300. The output of adder 170 is supplied to a second input of address selector 176. The offset overflow bit controls address selector 176. Thus, adder 170 and address selector 176 determine if the offset value causes the current fetch address to overflow to the next instruction cache page. The output of address selector 176 constitutes upper order bits (31:7) of a sequential address 320 following the next branch instruction. Low order bits (6:1) of sequential address 320 are obtained from an offset value 324 from BTB 110. A next target address 330, including bits (31:1), is also obtained from BTB 110. Address selector 230 receives sequential address 320 following the next branch instruction and next target address 330 at first and second inputs, respectively. Address selector 230 is controlled by the taken/not taken prediction from control logic 210 (FIG. 5), which may be from the prediction bits in branch target buffer 110 or from branch history table 162 (FIG. 5). In the case of a "taken" prediction, address selector 230 supplies next target address 330 as a next BTB address 350. In the case of a "not taken" prediction, address selector 230 supplies sequential address 320 as the next BTB address 350.

As shown in FIG. 6, block size calculation unit 240 includes a subtractor 310 and a comparator 360. The low order bits (7:1) of current fetch address 300 are supplied to a first input of subtractor 310. Subtractor 310 subtracts offset value 324 from the low order bits (7:1) of current fetch address 300. Comparison unit 360 determines if the output of subtractor 310 is less than 8. When the output of subtractor 310 is less than 8, instruction fetching is redirected to BTB 110. Otherwise, the current fetch address 300 is incremented by 8 bytes to determine the next fetch address. It will be understood that the value of 8 compared with the output of subtractor 310 is based on the number of bytes in a fetch buffer and that different predetermined values may be used within the scope of the invention.

Figure 7A:
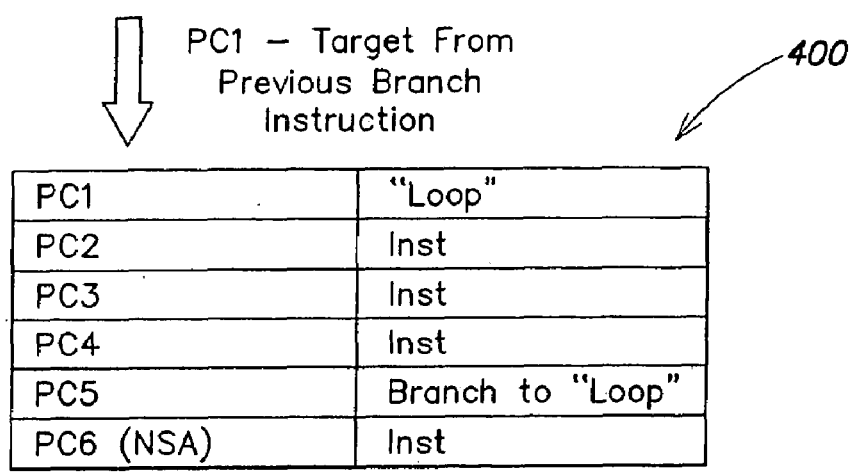
FIG. 7A illustrates an example of a program segment having a branch instruction.

A program segment including a program loop is illustrated in FIG. 7A. A program segment 400 includes instructions at addresses PC1 through PC6. A branch instruction at address PC5 branches to an instruction named "loop" at address PC1. An instruction at address PC6 is a next sequential address following the branch instruction.

Figure 7C:
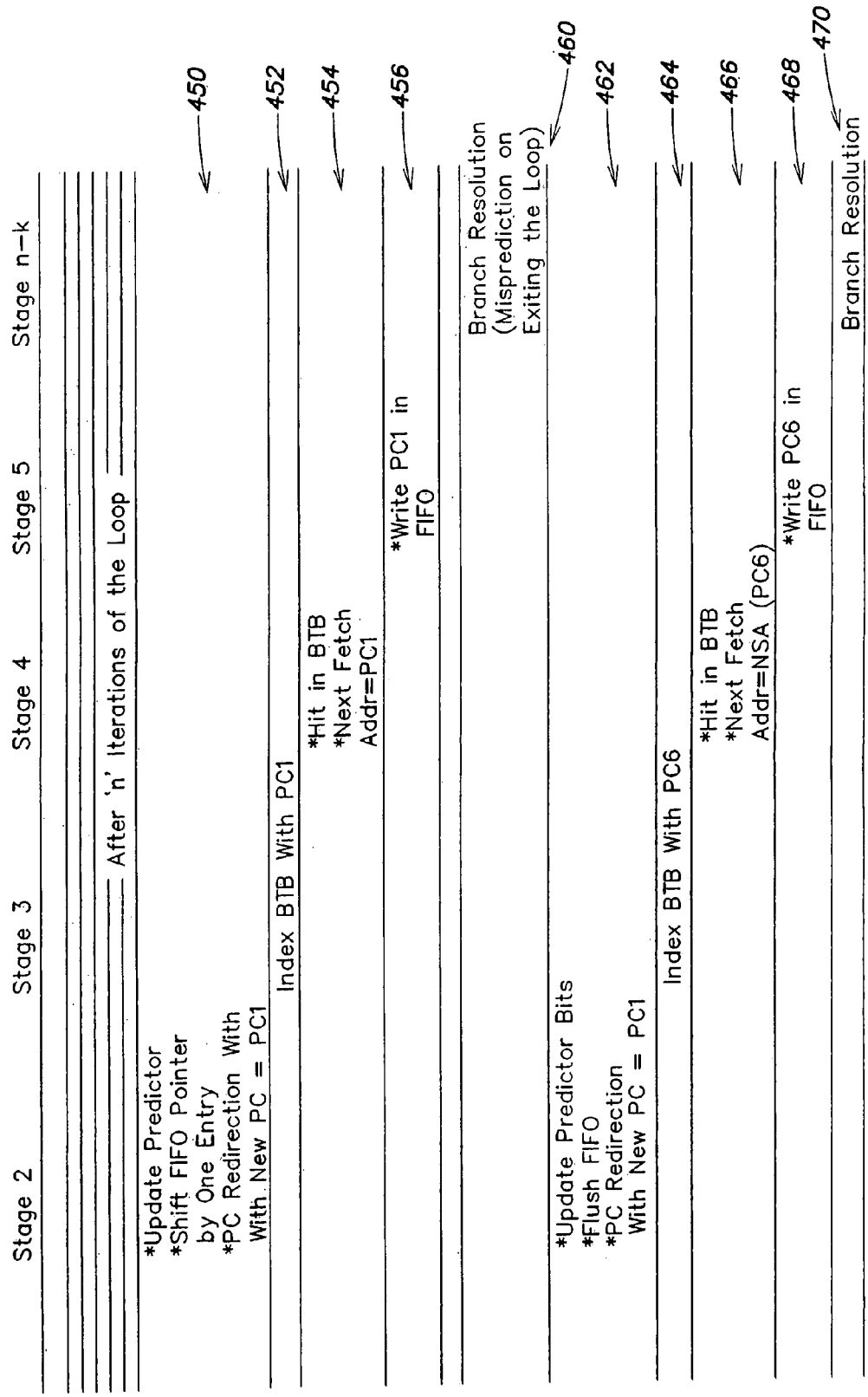

Execution of program segment 400 in a pipelined processor in accordance with an embodiment of the invention is illustrated in FIGS. 7B and 7C. In FIGS. 7B and 7C, operations in pipeline stages 1, 2, 3, 4, 5, n-k are shown from left to right, and time advances from top to bottom. As illustrated in FIG. 7A, the loop instruction at address PC1 is a target of a previous branch instruction. Referring to FIG. 7B, during clock cycle 410, instruction fetching is redirected to BTB address PC1 in stage 2. During clock cycle 412, the BTB 110 is indexed with address PC1 in stage 3. Since this is the first execution of the loop instruction, a miss occurs in the BTB in stage 4 during clock cycle 414, and the fetch address is the next sequential address. During clock cycle 416, address PC1 is written in the FIFO 74 in stage 5 and the BTB is disabled. Several cycles later, during clock cycle 420 the branch resolution unit 32 (stage n-k) determines a branch misprediction, thus incurring the misprediction penalty.

During clock cycle 422, the BTB is updated with the target address from the branch resolution unit, the prediction bits in BTB 110 are updated, FIFO 74 is flushed and instruction fetching is redirected to BTB address PC1 in stage 2. During clock cycle 424, the BTB is indexed with address PC1 in stage 3. During clock cycle 426, a hit occurs in the BTB, and the next fetch address is the target address from the BTB in stage 4. During clock cycle 428, address PC1 is written in FIFO 74 in stage 5. Several cycles later during clock cycle 430, branch resolution unit 32 (stage n-k) determines that the branch was predicted correctly.

During clock cycle 432, the prediction bits in BTB 110 are updated, a FIFO pointer is shifted by one entry and instruction fetching is redirected to BTB address PC1 in stage 2. During clock cycle 434, the BTB is indexed with address PC1 in stage 3. During clock cycle 436, a hit occurs in the BTB and the next fetch address is the target address (PC1) from the BTB in stage 4. During clock cycle 438, address PC1 is written in FIFO 74 in stage 5. Several cycles later during clock cycle 440, branch resolution unit 32 (stage n-k) determines that the branch was predicted correctly. The loop thus continues for a number of iterations.

The final iterations of the loop in program segment 400 are shown in FIG. 7C. During clock cycle 450, the prediction bits in BTB 110 are updated, the FIFO pointer is shifted by one entry and instruction fetching is redirected to BTB address PC1 in stage 2. During clock cycle 452, the BTB is indexed with address PC1 in stage 3. During clock cycle 454, a hit occurs in the BTB and the next fetch address is the target address (PC1) from the BTB in stage 4. During clock cycle 456, address PC1 is written in FIFO 74 in stage 5. Several cycles later during clock cycle 460, branch resolution unit 32 (stage n-a) determines a branch misprediction on exiting the loop, thus occurring the misprediction penalty.

During clock cycle 462, the prediction bits in BTB 110 are updated, the FIFO 74 is flushed and instruction fetching is redirected to BTB address PC1 in stage 2. During clock cycle 464, the BTB is indexed with address PC6 in stage 3. During clock cycle 466, a hit occurs in the BTB and the next fetch address is the next sequential address (PC6) in stage 4. During clock cycle 468, address PC6 is written in FIFO 74 in stage 5. During clock cycle 470, branch resolution occurs in stage n-k.

Figure 8:
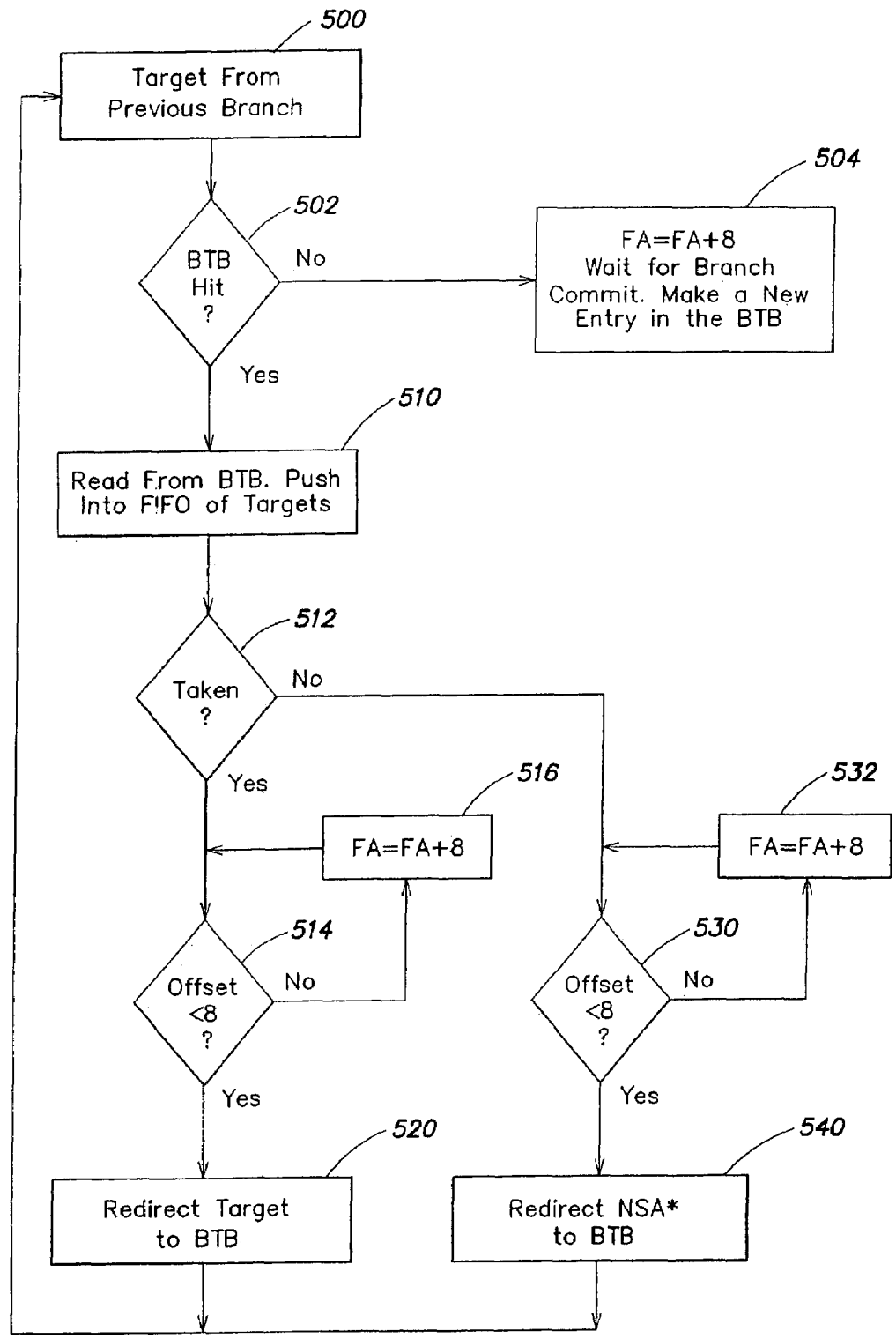
FIG. 8 is a flow diagram that illustrates operation of the branch target buffer in accordance with an embodiment of the invention.

A simplified flow diagram of instruction fetching utilizing the branch target buffer in accordance with an embodiment of the invention is shown in FIG. 8. In step 500, a target of a previous branch instruction is fetched by redirecting instruction fetching to the branch target buffer. The target address is supplied to the tag array of the BTB. If a BTB hit does not occur in step 502, the fetch address, FA, is incremented by 8 bytes in step 504 and the process waits for branch commit (branch resolution). Upon branch resolution, a new entry is made in the BTB in step 504. If a BTB hit occurs in step 502, the corresponding data entry is read from the BTB in step 510 and the data entry is written to FIFO 74 (FIG. 5). In step 512 the prediction bits in the data entry are used to determine if the branch is taken or not taken.

If the branch is taken, a determination is made in step 514 as to whether the difference between the fetch address and the offset value is less than 8 bytes. If the difference is not less than 8 bytes, the fetch address, FA, is incremented by 8 bytes in step 516 and instruction fetching proceeds with the incremented fetch address. The process then returns to step 514. If the difference between the fetch address and the offset value is less than 8 bytes, instruction fetching is redirected to the taken branch target address in step 520. The process then returns to step 502.

If a determination is made in step 512 that the branch is not taken, a determination is made in step 530 as to whether the difference between the fetch address and the offset value is less than 8 bytes. If the difference is not less than 8 bytes, the fetch address, FA, is incremented by 8 bytes in step 532 and instruction fetching proceeds with the incremented fetch address. The process then returns to step 530. If a determination is made in step 530 that the difference between the fetch address and the offset value is less than 8 bytes, instruction fetching is redirected to the next sequential address (NSA) in step 540. The process then returns to step 502.

Steps 514 and 530 correspond to the block size calculation performed by block size calculation unit 240 shown in FIGS. 5 and 6 and described above. As is apparent from FIG. 8, instruction fetching is redirected to the branch target buffer only when branch instructions occur in the program being executed, as determined by the block size calculation unit. Power saving is thereby realized in comparison with prior art branch caches which are accessed every cycle.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A method for branch prediction in a digital processor, comprising:
   providing a branch target buffer having a tag array and a data array, wherein each entry in the tag array provides an index to a corresponding entry in the data array;
   storing in a selected entry in the tag array a target address of a current branch instruction;
   storing in a corresponding entry in the data array a target address of a next branch instruction; and
   providing the target address of the next branch instruction in response to accessing the tag array with the target address of the current branch instruction.

2. A method as defined in claim 1, wherein storing a target address of a current branch instruction comprises storing a taken branch target address of the current branch instruction in the case of a taken branch.

3. A method as defined in claim 1, wherein storing a target address of a current branch instruction comprises storing an address of a next sequential instruction following the current branch instruction in the case of a not taken branch.

4. A method as defined in claim 1, wherein storing a target address of a next branch instruction comprises storing a taken branch target address of the next branch instruction and an offset value.

5. A method as defined in claim 4, wherein the offset value represents an address of a next sequential instruction following the next branch instruction.

6. A method as defined in claim 5, further comprising performing a block size calculation by subtracting the offset value from a current fetch address and redirecting instruction fetching to the branch target buffer when the difference between the offset value and the current fetch address is less than a predetermined value.

7. A method as defined in claim 6, wherein the predetermined value represents the length of a fetch buffer.

8. A method as defined in claim 1, wherein storing a target address of a next branch instruction further comprises storing prediction information corresponding to the next branch instruction.

9. A method as defined in claim 8, wherein storing a target address of a next branch instruction further comprises updating the prediction information following execution of the next branch instruction.

10. A method as defined in claim 8, further comprising selecting a taken branch target address of the next branch instruction or a next sequential address in response to the prediction information.

11. A method as defined in claim 1, wherein providing the target address of the next branch instruction comprises determining when the next branch instruction is to be executed in response to the target address of the next branch instruction.

12. A method as defined in claim 1, further comprising storing the target address of the next branch instruction in a buffer for use upon branch resolution of the current branch instruction.

13. A method as defined in claim 1, wherein storing a target address of a next branch instruction comprises storing a taken branch target address of the next branch instruction and a not taken branch target address of the next branch instruction.

14. Apparatus for predicting branches in a program executed on a digital processor, comprising:
a branch target buffer having a tag array and a data array, wherein each entry in the tag array provides an index to a corresponding entry in the data array;
means for storing in a selected entry in the tag array a target address of a current branch instruction;
means for storing in a corresponding entry in the data array a target address of a next branch instruction; and
means for providing from the branch target buffer the target address of the next branch instruction in response to accessing the tag array with the target address of the current branch instruction.

15. Apparatus as defined in claim 14, wherein said means for storing a target address of a current branch instruction comprises means for storing a taken branch target address of the current branch instruction in the case of a taken branch.

16. Apparatus as defined in claim 14, wherein said means for storing a target address of a current branch instruction comprises means for storing an address of a next sequential instruction following the current branch instruction in the case of a not taken branch.

17. Apparatus as defined in claim 14, wherein said means for storing a target address of a next branch instruction comprises means for storing a taken branch target address of the next branch instruction and an offset value.

18. Apparatus as defined in claim 17, wherein the offset value represents an address of a next sequential instruction following the next branch instruction.

19. Apparatus as defined in claim 14, wherein said means for storing a target address of a next branch instruction comprises means for storing a taken branch target address of the next branch instruction and a not taken branch target address of the next branch instruction.

20. Apparatus as defined in claim 18, further comprising a block size calculation unit for subtracting the offset value from a current fetch address and for redirecting instruction fetching to the branch target buffer when the difference between the offset value and the current fetch address is less than a predetermined value.

21. Apparatus as defined in claim 20, wherein the predetermined value represents the length of a fetch buffer.

22. Apparatus as defined in claim 21, wherein the block size calculation unit comprises a subtractor for subtracting the offset value from the current fetch address and a comparator for redirecting instruction fetching to the branch target buffer when the difference between the offset value and the current fetch address is less than the predetermined value.

23. Apparatus as defined in claim 14, wherein said means for storing a target address of a next branch instruction comprises means for storing prediction information corresponding to the next branch instruction.

24. Apparatus as defined in claim 23, wherein said means for storing a target address of a next branch instruction further comprises means for updating the prediction information following execution of the next branch instruction.

25. Apparatus as defined in claim 23, further comprising means for selecting a taken branch target address of the next branch instruction or a next sequential address in response to the prediction information.

26. Apparatus as defined in claim 14, further comprising a buffer for storing the target address of the next branch instruction for use upon branch resolution of the current branch instruction.

27. Apparatus for predicting branches in a program executed on a digital processor, comprising:
a branch target buffer having a tag array and a data array, wherein each entry in the tag array provides an index to a corresponding entry in the data array, wherein a selected entry in the tag array stores a target address of a current branch instruction and a corresponding entry in the data array stores a taken branch target address of a next branch instruction, a not taken branch target address of the next branch instruction and prediction information corresponding to the next branch instruction;
an address selector for selecting the taken branch target address or the not taken branch target address in response to the prediction information; and
a block size calculation unit for redirecting instruction fetching to the branch target buffer when the difference between the not taken branch target address and the current fetch address is less than a predetermined value.

28. Apparatus as defined in claim 27, wherein the not taken branch target address comprises an address of a next sequential instruction following the next branch instruction.

29. Apparatus as defined in claim 27, wherein the block size calculation unit comprises a subtractor for subtracting the not taken branch target address from the current fetch address and a comparator for redirecting instruction fetching to the branch target buffer when the difference between the not taken branch target address and the current fetch address is less than the predetermined value.

30. Apparatus as defined in claim 27, further comprising a buffer for storing the target address of the next branch instruction for use upon branch resolution of the current branch instruction.

* * * * *